(12) United States Patent
Fadler et al.

(10) Patent No.: US 6,513,973 B1
(45) Date of Patent: Feb. 4, 2003

(54) X-RAY DIAGNOSTIC DEVICE WITH A POSITIONING PLATE FOR AN EXAMINATION SUBJECT ADJUSTABLE AT A BASE

(75) Inventors: Franz Fadler, Hetzles (DE); Karl Heinz Kaul, Neunkirchen (DE); Stefan Leidenberger, Effeltrich (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/595,419

(22) Filed: Jun. 16, 2000

(30) Foreign Application Priority Data

Jun. 17, 1999 (DE) .......................................... 199 27 756

(51) Int. Cl.⁷ ................................................. G21K 4/00
(52) U.S. Cl. ........................................ 378/190; 378/196
(58) Field of Search ................................. 378/189, 190, 378/196

(56) References Cited

U.S. PATENT DOCUMENTS

| 2,668,912 A | * | 2/1954 | Goldfield et al. ............ 378/196 |
| 4,618,133 A | | 10/1986 | Siczek |
| 5,949,848 A | * | 9/1999 | Gilblom ...................... 378/98.8 |

FOREIGN PATENT DOCUMENTS

| DE | 44 32 448 | 8/1998 |
| EP | 0761166 | 6/1996 |

* cited by examiner

Primary Examiner—Craig E. Church
(74) Attorney, Agent, or Firm—Schiff Hardin & Waite

(57) ABSTRACT

An x-ray diagnostic device having a positioning plate for an examination subject mounted to as to be adjustable at a base has a radiation receiver implemented as a solid state detector that is mounted at the base via a gallows frame so as to be adjustable with respect to the positioning plate.

14 Claims, 2 Drawing Sheets

X-RAY DIAGNOSTIC DEVICE WITH A POSITIONING PLATE FOR AN EXAMINATION SUBJECT ADJUSTABLE AT A BASE

BACKGROUND OF THE INVENTION

1. Field of the Invention

The present invention is directed to an x-ray diagnostic device of the type having a base and a positioning plate for an examination subject, the positioning plate being adjustable at the base.

2. Description of the Prior Art

U.S. Pat. No. 4,618,133 discloses an x-ray diagnostic device having a positioning plate for an examination subject that is adjustably seated at a base. The positioning plate can be turned around a horizontal axis via the base and is mounted so as to be adjustable along its longitudinal axis relative to the base. An exposure unit, allocated to the positioning plate, has an x-ray image intensifier and a radiation emitter which are mounted at the ends of a C-arm. The C-arm is adjustable along its circumference and is mounted at the, base via a holder. By means of the holder, the C-arm can be adjusted in directions toward or away from the positioning plate.

An x-ray diagnostic device having a positioning plate mounted so as to be adjustable at a base and having a radiation receiver seated at the base is disclosed in European Application 0 761 166. The radiation receiver is implemented as a detector line and arranged at a C-arm which is adjustable relative to the base.

An x-ray diagnostic device is known from German PS 44 32 448, wherein a positioning plate for an examination subject as well as an aiming device are adjustably seated at a base. The positioning plate is adjustably mounted flush at the base as well as to allow rotation around a rotational axis at the base. The aiming device sits at the base at a level parallel to the positioning plate and can be adjusted vertically at a column.

SUMMARY OF THE INVENTION

An object of the present invention is to provide an x-ray diagnostic device of the type described in German PS 44 32 448 with respect to accessibility to the positioning plate, while maintaining a compact structure which is versatilely applicable.

This object is inventively achieved in an x-ray diagnostic device in accordance with the invention wherein the radiation receiver is a solid-state detector and is adjustably seated at a gallows frame with respect to the positioning plate, the positioning plate (for an examination subject) being adjustable at a base and the radiation receiver also being mounted (via the gallows) at the base. Solid state detectors exhibit a compact structure in comparison to the use of an image intensifier. By means of the solid state detector adjustably seated at a gallows frame with respect to the positioning plate, access to the positioning plate is also particularly improved, compared to known systems, due to the flat construction style. In addition, a broader field of use arises; radioscopy techniques and recording techniques, for example, can also be advantageously performed.

It is particularly advantageous to mount the radiation receiver at the gallows frame so as to be adjustable around three spatial axes, so that the x-ray exposures of an examination subject can be made from various radioscopic directions.

In an embodiment the radiation receiver is mounted at one end of a first gallows frame arm that is oriented substantially horizontally. As a result of the adjustability around the spatial axes, the surface of the radiation receiver then can be adjusted not only substantially parallel to the positioning plate as in the prior art, but also can be adjusted substantially vertically relative to the positioning plate.

In order to further increase the adjustment and orientation possibilities of the radiation receiver, the first gallows frame arm is mounted (adjustable along its longitudinal axis) at a second gallows frame arm that is oriented substantially vertically to the first.

Compared to known x-ray diagnostic devices, it is of further advantage when the first gallows frame arm is adjustably mounted along the second gallows frame arm, since the radiation receiver then can be arranged by corresponding adjustment not only above but also below the positioning plate.

If the gallows frame arm is adjustably mounted along the positioning plate, then not only head but also abdominal or leg exposures can be prepared, without an adjustment of the positioning plate being required. The same area of an examination subject also can be examined from different exposure orientations, when the positioning plate is adjustably seated along its longitudinal and/or transverse axis.

A particularly compact structure of the x-ray diagnostic device results when the positioning plate and the gallows frame are mounted via a common holder at the base.

In an embodiment wherein the holder at the base is adjustable, particularly in height and/or around a rotational axis, then an examination subject arranged on the positioning plate can be brought into a position or orientation favorable for the treatment or examination.

Particularly versatile examinations on an examination subject arranged on the positioning plate can be performed in an embodiment wherein the positioning plate is mounted so as to be adjustable along its longitudinal axis with respect to the holder and/or in a direction substantially vertically to its longitudinal axis.

In view of the arrangement of the radiation receiver below the positioning plate, besides the adjustability of the receiver at the gallows frame, it is expedient to mount the positioning plate so as to also be adjustable with respect to the holder in a direction substantially vertical to its surface. Thus, additional space can be made for the radiation receiver below the positioning plate, in addition to which a compact structure of the x-ray diagnostic device is achieved.

DESCRIPTION OF THE PREFERRED EMBODIMENTS

Figure 1:
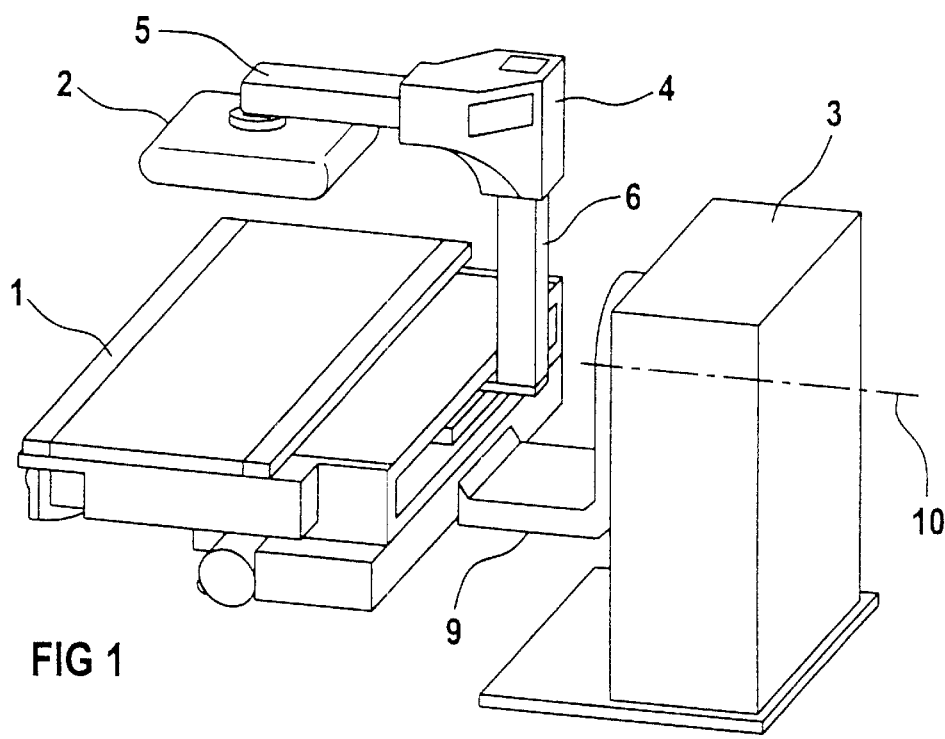
FIGS. 1 and 2 are two perspective views of an inventive x-ray diagnostic device.

In the figures, identical elements are identified with the same reference characters.

Figure 2:
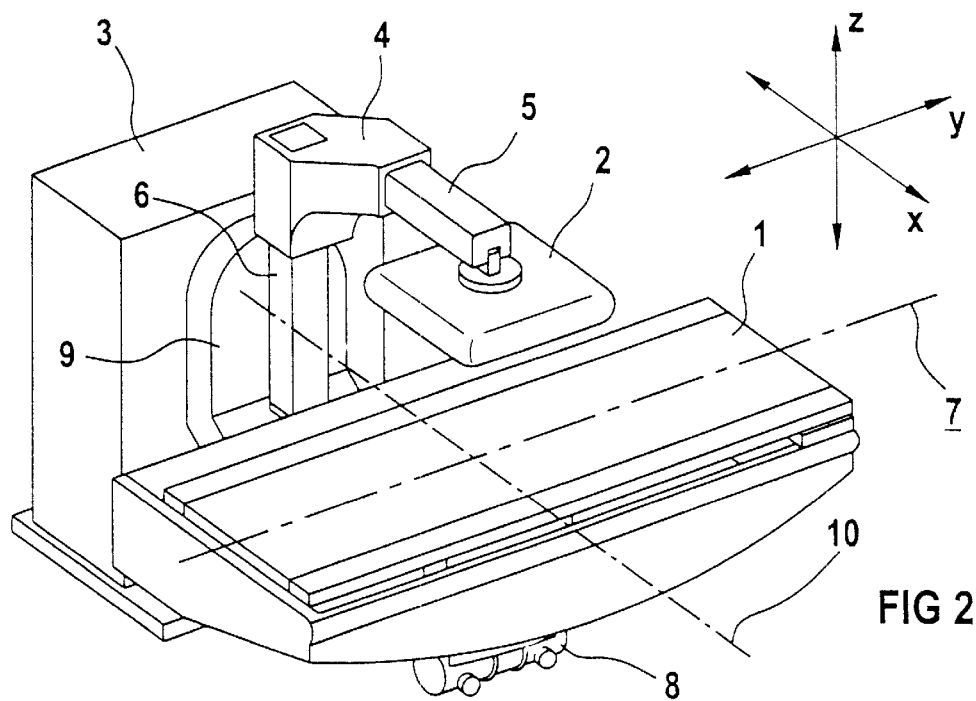
Figure 3:
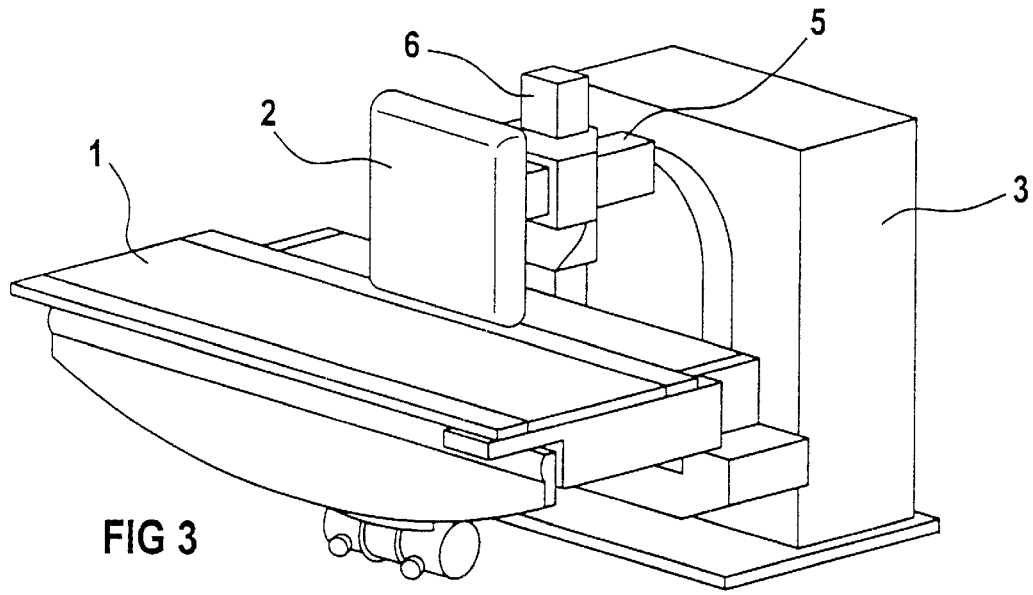
FIG. 3 shows the x-ray diagnostic device according to FIGS. 1 and 2 with a radiation receiver oriented substantially vertically to the surface of the positioning plate.

An exemplary embodiment of an x-ray diagnostic device in conformity with the invention is shown in FIGS. 1 and 2.

The inventive x-ray diagnostic device has a positioning plate 1 for an examination subject as well as a radiation receiver 2 that are mounted at a base 3. The radiation receiver 2 is a solid state detector and is mounted at a gallows frame 4 so as to be adjustable with respect to the positioning plate 1. The radiation receiver 2 can, as proceeds from FIG. 2, be mounted for this purpose at a first end of a first gallows frame arm 5 oriented substantially horizontally, so as to be adjustable around the orthogonal axes x, y and z. In order to further increase the adjustability of the radiation receiver 2, the first gallows frame arm 5 can be mounted to be adjustable along its longitudinal axis and along a longitudinal axis of a second gallows frame arm 6 oriented substantially vertically to the first arm 5. Via the first gallows frame arm 5, the radiation receiver 2 is thus adjustable in a direction essentially vertical to the longitudinal axis 7 of the positioning plate 2. The distance between the radiation receiver 2 and the positioning plate 1 can be set by adjustment along the second gallows frame arm 6. The magnification scale also can be changed, for example, when a radiation emitter 8 is arranged below the positioning plate 1. It further proceeds from FIGS. 1 and 2 that the positioning plate 1 and/or the radiation receiver 2 are mounted via the gallows frame 4 at a holder 9 at the base 3. Swivelling around a rotational axis 10 can be effected via the holder 9. In addition, it is possible to adjust the holder 9, and thus the positioning plate 1 and the radiation receiver 2 in a vertical direction via a lifting means that is arranged at the base 3 which engages the holder 9. In the scope of the invention, the positioning plate 1 can be seated to be adjustable not only along its longitudinal axis 7, but also along its transverse axis. In FIG. 1 it can be seen that the gallows frame 4 can be adjustably seated at guides along the positioning plate 3 at the holder 9.

Figure shows 3 that the radiation receiver 2 can be adjusted in a vertical position by means of swivelling around the x-axis with respect to the surface to the positioning plate 1, so that an examination subject can also be irradiated from the side using a separate radiation emitter for the preparation of an x-ray exposure.

Figure 4:
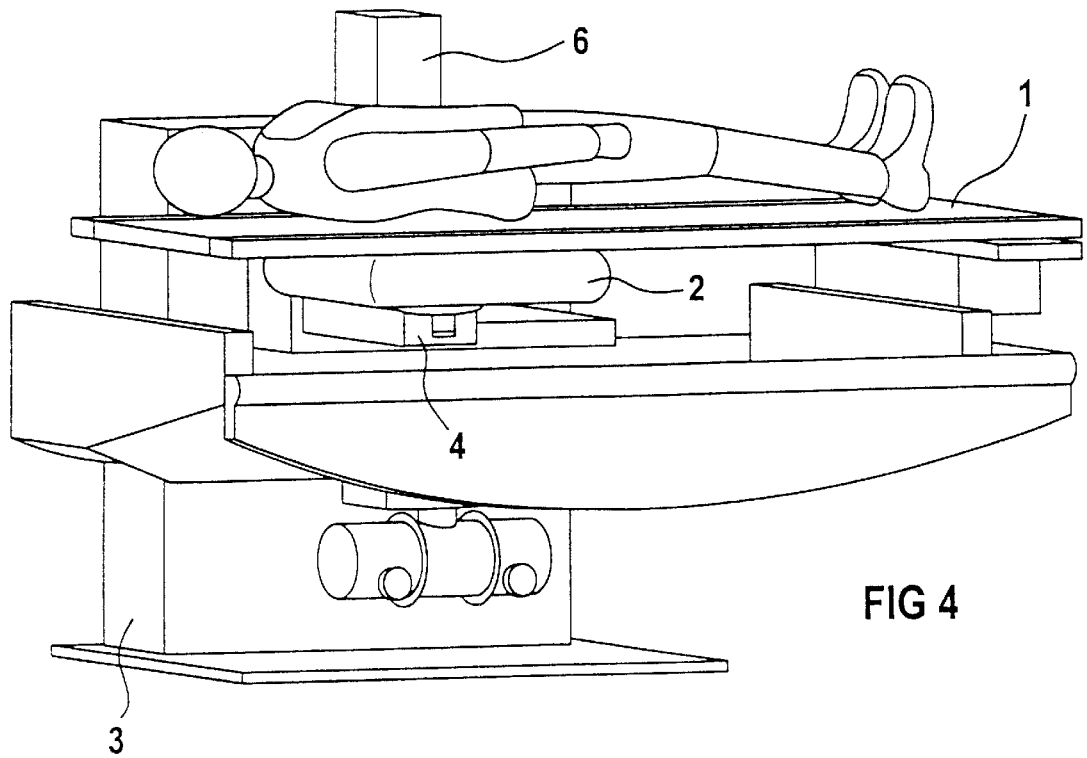
FIG. 4 shows the x-ray diagnostic device according to the FIGS. 1 and 2 with a radiation receiver arranged below the positioning plate.

FIG. 4 shows how a height adjustment of the positioning plate 1 with respect to the holder 9 allows the radiation receiver 2 to be brought into a position below the positioning plate 1 by rotation around the x-axis and adjustment along the first and second gallows frame arms 5 and 6. An x-ray exposure also can be prepared using a separate radiation emitter, with the separate radiation emitter arranged above the positioning plate 1 and above the examination subject. Such a height adjustment of the positioning plate 1 is, however, only required if not enough room is provided for the radiation receiver 2 below the positioning plate 1.

The positioning plate 1 can be brought into a vertical position by means of swivelling and raising the holder 9, wherein so-called wall exposures, i.e. examinations of a standing patient can be performed. Furthermore, it is possible to bring the examination subject into a head exposure position by swivelling in an opposite direction, in order to allow specific x-ray exposures to be prepared.

By means of the invention, an x-ray diagnostic device is achieved that allows good accessibility and versatile applicability with a compact structure. Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray diagnostic device comprising:

base;

a positioning plate, adapted to receive an examination subject, adjustably mounted at said base;

a gallows frame adjustably mounted at said base so as to be selectively positionable relative to said positioning plate, said gallows frame having a first gallows arm, to which said solid state detector is mounted, said first gallows arm being substantially horizontally oriented, and a second gallows arm, oriented substantially vertically relative to said first gallows arm, with said first gallows arm having a longitudinal axis and being mounted to said second gallows arm so as to be adjustable along said longitudinal axis; and a solid state detector for x-rays adjustably mounted at said gallows frame.

2. An x-ray diagnostic device as claimed in claim 1 wherein said solid state detector is mounted at said gallows so as to be adjustable in three orthogonal axes.

3. An x-ray diagnostic device as claimed in claim 1 wherein said solid state detector is adjustable via said gallows frame from a position above said positioning plate into a position below said positioning plate.

4. An x-ray diagnostic device as claimed in claim 1 wherein said gallows frame is adjustably mounted at said base for movement along said positioning plate.

5. An x-ray diagnostic device as claimed in claim 1 wherein said first gallows arm additionally is adjustable along said second gallows arm.

6. An x-ray diagnostic device as claimed in claim 1 further comprising a common holder disposed at said base, to which both said positioning plate and said gallows frame are mounted.

7. An x-ray diagnostic device as claimed in claim 6 wherein said holder is adjustably mounted at said base.

8. An x-ray diagnostic device as claimed in claim 7 wherein said holder is adjustable relative to said base around a rotational axis.

9. An x-ray diagnostic device as claimed in claim 7 wherein said holder is adjustable in height relative to said base.

10. An x-ray diagnostic device as claimed in claim 6 wherein said solid state detector is also mounted at said holder, below said positioning plate.

11. An x-ray diagnostic device as claimed in claim 6 wherein said positioning plate has a longitudinal axis, and wherein said positioning plate is adjustable at said holder along said longitudinal axis.

12. An x-ray diagnostic device as claimed in claim 6 wherein said positioning plate has a positioning plate surface, and wherein said positioning plate is adjustable at said holder in a direction substantially vertical to said positioning plate surface.

13. An x-ray diagnostic device as claimed in claim 6 wherein said positioning plate has a longitudinal axis, and wherein said positioning plate is mounted at said holder so as to be adjustable in a direction substantially vertically to said longitudinal axis.

14. An x-ray diagnostic device as claimed in claim 13 wherein said positioning plate is also adjustable at said holder in a direction substantially along said longitudinal axis.

* * * * *